US006849087B1

(12) United States Patent
Chuter

(10) Patent No.: US 6,849,087 B1
(45) Date of Patent: Feb. 1, 2005

(54) DEVICE AND METHOD FOR STAGED IMPLANTATION OF A GRAFT FOR VASCULAR REPAIR

(76) Inventor: Timothy A. M. Chuter, 70 Valley Ct., Atherton, CA (US) 94027

(*) Notice: Subject to any disclaimer, the term of this patent is extended or adjusted under 35 U.S.C. 154(b) by 68 days.

(21) Appl. No.: 09/684,008

(22) Filed: Oct. 6, 2000

Related U.S. Application Data

(60) Provisional application No. 60/157,985, filed on Oct. 6, 1999.

(51) Int. Cl.$^7$ .................................................. A61F 2/06
(52) U.S. Cl. .................... 623/1.23; 623/1.13; 623/1.35; 623/1.36; 623/903; 606/108; 606/194; 128/898
(58) Field of Search ................................ 623/1.34, 1.1, 623/1.11, 1.13, 1.14, 1.23, 1.35, 1.36, 902, 903; 606/108, 191, 192, 194, 195, 198; 128/898

(56) References Cited

U.S. PATENT DOCUMENTS

| | | |
|---|---|---|
| 4,140,126 A | 2/1979 | Choudhury |
| 4,617,932 A | 10/1986 | Kornberg |
| 4,872,874 A | 10/1989 | Taheri |
| 4,994,071 A | 2/1991 | MacGregor |
| 5,071,407 A | 12/1991 | Termin et al. |
| 5,078,720 A | 1/1992 | Burton et al. |
| 5,078,726 A | 1/1992 | Kreamer |
| 5,104,399 A | 4/1992 | Lazarus |
| 5,116,318 A | 5/1992 | Hillstead |
| 5,123,917 A | 6/1992 | Lee |
| 5,151,105 A | 9/1992 | Kwan-Gett |
| 5,207,695 A | 5/1993 | Trout, III |
| 5,211,658 A | 5/1993 | Clouse |
| 5,211,683 A | 5/1993 | Maginot |
| 5,219,355 A | 6/1993 | Parodi et al. |
| 5,282,824 A | 2/1994 | Gianturco |
| 5,290,295 A | 3/1994 | Querals et al. |
| 5,316,023 A | 5/1994 | Palmaz et al. |
| 5,330,500 A | 7/1994 | Song |
| 5,330,528 A | 7/1994 | Lazim |
| 5,354,308 A | 10/1994 | Simon et al. |
| 5,360,443 A | 11/1994 | Barone et al. |
| 5,370,683 A | 12/1994 | Fontaine |
| 5,387,235 A | 2/1995 | Chuter |
| 5,425,765 A | 6/1995 | Tiefenbrun et al. |
| 5,464,449 A | 11/1995 | Ryan et al. |
| 5,489,295 A | 2/1996 | Piplani et al. |
| 5,507,769 A | 4/1996 | Marin et al. |
| 5,527,355 A | 6/1996 | Ahn |
| 5,562,727 A | 10/1996 | Turk et al. |
| 5,571,172 A | 11/1996 | Chin |

(List continued on next page.)

Primary Examiner—David J. Isabella
Assistant Examiner—Urmi Chattopadhyay
(74) Attorney, Agent, or Firm—William G. Lane

(57) ABSTRACT

A graft for repairing defects in arteries is formed from a flexible graft and at least one attachment system. A device and method is disclosed for implanting a graft within the vasculature of a patient, in which the graft is inserted into the patient at a different stage than the attachment systems, and which allows for direct percutaneous insertion of the graft and attachment systems. The method permits control over the position of the graft in the vasculature during the course of deployment of the graft and attachment systems by providing for traction forces to be applied to opposing ends of the graft.

3 Claims, 17 Drawing Sheets

U.S. PATENT DOCUMENTS

| | | |
|---|---|---|
| 5,575,817 A | 11/1996 | Martin |
| 5,591,195 A | 1/1997 | Taheri et al. |
| 5,591,228 A | 1/1997 | Edoga |
| 5,609,627 A | 3/1997 | Goicoechea et al. |
| 5,628,788 A | 5/1997 | Pinchuk |
| 5,632,763 A | 5/1997 | Glastra |
| 5,662,614 A | 9/1997 | Edoga |
| 5,676,696 A | 10/1997 | Marcade |
| 5,676,697 A | 10/1997 | McDonald |
| 5,683,451 A | 11/1997 | Lenker et al. |
| 5,693,088 A | 12/1997 | Lazarus |
| 5,707,378 A | 1/1998 | Ahn et al. |
| 5,713,917 A | 2/1998 | Leonhardt et al. |
| 5,755,770 A | 5/1998 | Ravenscroft |
| 5,755,777 A | 5/1998 | Chuter |
| 5,800,514 A | 9/1998 | Nuñez et al. |
| 5,800,521 A | 9/1998 | Orth |
| 5,824,036 A | 10/1998 | Lauterjung |
| 5,824,037 A | 10/1998 | Fogarty et al. |
| 5,824,039 A | 10/1998 | Piplani et al. |
| 5,824,040 A | 10/1998 | Cox et al. |
| 5,824,055 A | 10/1998 | Spiridigliozzi |
| 5,843,162 A * | 12/1998 | Inoue .................. 623/1.13 |
| 5,851,228 A | 12/1998 | Pinheiro |
| 5,855,597 A | 1/1999 | Jayaraman |
| 5,855,598 A | 1/1999 | Pinchuk |
| 5,860,998 A | 1/1999 | Robinson et al. |
| 5,871,536 A | 2/1999 | Lazarus |
| 5,925,076 A | 7/1999 | Inoue |
| 5,948,017 A | 9/1999 | Taheri |
| 5,961,548 A | 10/1999 | Shmulewitz |
| 5,993,481 A | 11/1999 | Marcade et al. |
| 6,070,589 A | 6/2000 | Keith et al. |
| 6,099,558 A | 8/2000 | White et al. |

* cited by examiner

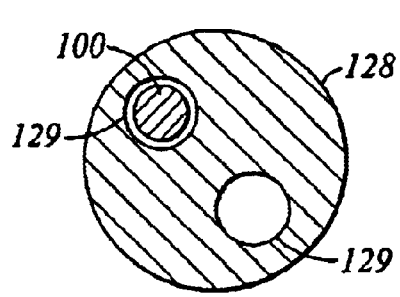
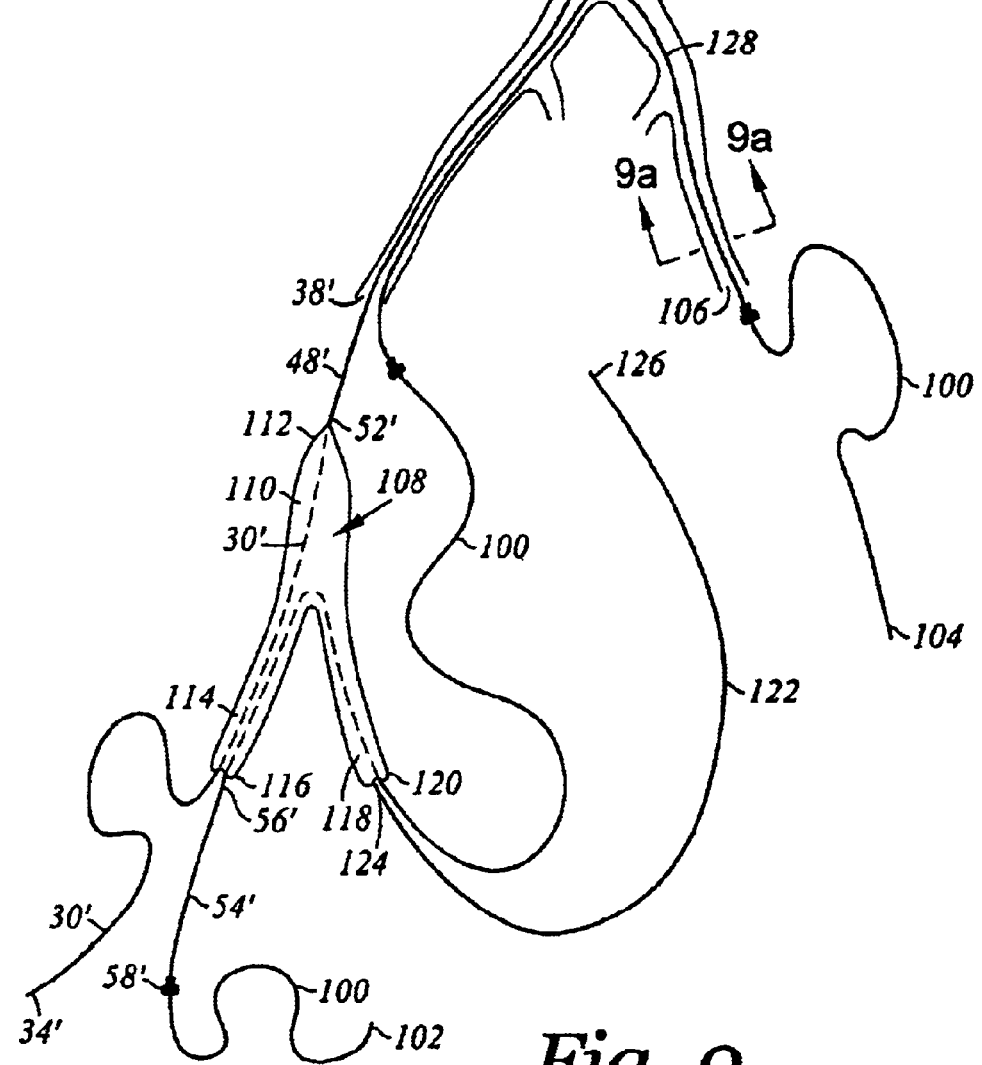

DEVICE AND METHOD FOR STAGED IMPLANTATION OF A GRAFT FOR VASCULAR REPAIR

This application is based on U.S. Provisional Application No. 60/157,985 filed Oct. 6, 1999.

FIELD OF THE INVENTION

The present invention relates to intraluminal grafts and their attachment systems which are used for repairing defects in vessels and other lumens within the body. More particularly, the present invention relates to systems for forming linear and bifurcated grafts and to methods for delivering such grafts and their attachment systems to the correct position within the defective body lumen by staged implantation.

BACKGROUND OF THE INVENTION

Aneurysms are discrete dilations of the arterial wall. One of the most common, and among the most life threatening, is an aneurysm of the abdominal aorta between the renal and iliac arteries. If untreated, the aneurysm dilates progressively with an ever increasing risk of rupture and hemorrhagic death.

One method of treatment is provided by direct surgical intervention, in which the defective vessel may be bypassed or replaced using a prosthetic device such as a synthetic graft. The risks involved in direct surgical intervention of this magnitude are great, and include an extensive recovery period.

In recent years a less invasive method of treatment has evolved through a series of inventions. The details vary, but, conventionally, a resilient tubular conduit (herein referred to as a "graft") is introduced into the defective vessel by means of catheters introduced into the femoral artery, and is attached to the non-dilated arteries above and below the aneurysm using expandable metallic or plastic cylinders (herein referred to as "attachment systems").

However, the use of generally cylindrical grafts to reinforce vascular walls in a patient is not without problems. The known methods for delivering grafts to the required location within a patient's vascular system conventionally require that an attachment system be delivered simultaneously with the graft, axially overlapping the graft and located either on the interior or the exterior of the graft's lumen, so that upon deployment of the graft the attachment system is expanded to attach the graft to the vascular wall. In the prior art, the attachment system is typically connected to the graft before implantation in the patient by means such as stitching. Because grafts are conventionally required to be compressed into a capsule or sheath before being implanted in final position within the patient's vascular system, delivery capsules or sheaths must be sufficiently small to enable insertion into the patient's vessel, and, once inserted, must be sufficiently flexible to allow bending around corners and branches of the patient's vascular tree. Yet, as a consequence of the practice of delivering the attachment system simultaneously with and axially overlapping the graft, the outer diameter of the delivery capsule or sheath containing the compressed graft in such cases is increased by the presence of the compressed attachment system.

One of the problems encountered in the art of delivering grafts to the vascular system of a patient is that complications may be encountered in maneuvering the compressed graft and its delivery system around the bends and branches of the patient's vascular system. It will be appreciated that the greater the outer dimension of the capsule containing the compressed graft to be delivered, the more inflexible it will be, making delivery to the final destination more difficult and perhaps even impossible in some patients.

Another problem encountered in the art of graft delivery is that, in the majority of cases, the patient must be subject to surgery in which the appropriate vessel is surgically exposed and opened by incision to allow entry of the graft. Significantly, it is this surgical procedure on the vessel which gives rise to the most serious complications known in the art of minimally invasive graft delivery, with complications taking the form of infection, patient discomfort, and necrosis of the vessel itself. However, if the outside dimension of the delivery capsule were sufficiently small, it might be possible, depending on the size and condition of the patient, to insert the capsule into the patient's vessel by applying sufficient force to the skin and artery of the patient with a sharpened end of the graft's delivery capsule, similar to the commonly known method of inserting a needle directly into the vein or artery of a patient.

There therefore exists a need to reduce the outside dimension of the capsule or sheath containing a compressed graft to be delivered to the patient's vascular system. This invention addresses these needs.

SUMMARY OF THE INVENTION

The present invention provides a device and a method for delivering a graft to a desired location within a patient's vascular system, and then, while maintaining the graft's position by applying traction forces to the ends of the graft, to deliver at least one attachment system for attaching the graft to the vascular wall. By delivering the graft and the attachment system in separate stages, the outside dimensions of the delivery capsules or sheaths containing the graft and the attachment system separately may be substantially less than that of a capsule or sheath containing the graft and the attachment system together. This reduction in outside dimension of the delivery capsule or sheath facilitates delivery of the graft and may allow for the direct percutaneous insertion of the graft and its attachment system, depending on the condition of the patient.

One aspect of the present invention provides a device and a method for repairing a linear vascular structure. A method in accordance with this aspect of the present invention includes the use of a linear graft compressible between an uncompressed condition and a compressed condition, a guide-wire, an upstream traction catheter and a downstream traction catheter, and at least one attachment system compressible radially between an expanded condition and a compressed condition. The guidewire may be placed to run between a first access point in the vascular structure located superior to the defective portion of the vessel to be repaired, and a second access point located inferior to the defective portion of the vessel. By using the traction catheters releasably connected to the graft, the graft in a compressed condition is fed over the guidewire to a desired position within the vascular structure, whereupon the graft is released from its compressed condition to revert toward its uncompressed condition. While maintaining the graft in a desired position by applying traction forces through the traction catheters to both ends of the graft, at least one attachment system in compressed condition is fed over the guidewire to a desired position within the graft, whereupon the attachment system is expanded to its expanded condition. In the preferred embodiment, all elements of the repair are introduced into the vascular system by direct percutaneous insertion. When the required number of attachment systems have been inserted and expanded within the graft, the traction catheters are released from the graft and are withdrawn from the vascular system together with the guidewire, leaving the graft attached to the vascular wall.

Another aspect of the present invention provides a device and a method for repairing, by direct percutaneous delivery of the graft and attachment system, a bifurcated vascular structure having an aortic branch and left and right iliac branches projecting from the aortic branch at a point of bifurcation. A method in accordance with this aspect of the present invention includes the use of a bifurcated graft foldable between an uncompressed condition and a compressed condition and having a superior trunk and left and right inferior legs or leg portions projecting from the superior trunk at a point of bifurcation, a first and a second guidewire, an upstream traction catheter, a left downstream and a right downstream traction catheter, and at least one attachment system, compressible radially between an expanded condition and a compressed condition. The first guidewire is configured to run between a first access point superior to the aortic branch of the vascular structure and a second access point inferior to one of the iliac branches of the vascular structure. The second guide wire is configured to run between the second access point and a third access point inferior to the other iliac branch of the vascular structure. By using the upstream traction catheter releasably connected to the graft, the graft in a compressed condition is fed over the first guidewire to a desired position within the vascular structure. By using the left and right downstream traction catheters releasably connected to the left and right inferior legs of the graft respectively, the left and right inferior legs of the graft may be pulled into the left and right iliac branches of the vascular structure. Once located at the desired position within the vascular system, the graft may be released from its compressed condition. While maintaining the graft in its desired position by applying appropriate tension to at least one traction catheter, at least one attachment system in compressed condition may be fed over one of the guidewires to a desired position within the graft, whereupon the attachment system may be expanded or allowed to expand. When the required number of attachment systems have been inserted and expanded within the graft, the traction catheters are released from the graft and are withdrawn from the vascular system together with the guidewires, leaving the bifurcated graft attached to the vascular wall. In the preferred embodiment, all elements of the repair are introduced into the vascular system by direct percutaneous insertion.

By allowing the graft to be delivered at a different stage than the attachment system (or attachment systems), the diameter of the capsule or sheath delivering the graft may be reduced. Furthermore, it will be appreciated that, because the graft of the present invention may be pulled, rather than pushed, into position, the delivery capsule does not suffer adversely from the reduced resistance to kinking which otherwise follows from its reduced diameter. On the contrary, the reduction in diameter of the delivery capsule, combined with its placement by a traction force, allows greater flexibility which has the advantage of facilitating delivery of the graft through the branches of the vascular system. It also has the advantage, in suitable cases, of permitting delivery of the graft by a direct percutaneous insertion, without the need for a further surgical procedure to provide access into the vascular system of the patient. If such a surgical procedure can be avoided, it may be possible to use the procedure of minimally invasive luminal repair in a wider range of situations by a wider range of medical personnel. For example, it may be used as an outpatient procedure in which the patient is not hospitalized. It will be appreciated that outpatient treatment in this context will be considerably less costly than inpatient treatment to achieve the same result, and will be substantially more convenient for the patient.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 3a is a sectional view of the releasable connection between the; collection catheter and the upstream traction catheter;

FIG. 6a is a cross-sectional view of the delivery assembly of FIG. 6, showing an attachment system contained in a compressed condition by a sheath, and releasably connected to a pushrod;

FIG. 9 is a schematic view showing the first and second guidewires of FIG. 8 and their relationship to a bifurcated graft and upstream and downstream traction catheters, before they are introduced into the vascular system; a relay catheter is also shown, threaded over the second guidewire entering the vascular system from the third access point and exiting at the second access point;

FIG. 9a is a sectional view through the relay catheter of FIG. 9 after it has been passed over the second-guidewire, and showing an empty lumen ready to receive the left downstream traction catheter.

FIG. 11a is a sectional view of the right downstream traction catheter, showing the second guidewire threaded through a lumen;

DETAILED DESCRIPTION OF THE PREFERRED EMBODIMENTS

The device and method disclosed by the present invention may be used to deliver to a patient's vascular system a flexible tubular graft which may be straight, tapered, or bifurcated. In the preferred embodiment of this invention, the graft may be delivered to the patient's vascular system without performing surgery on the patient to open the vessel prior to insertion of the graft; rather, insertion is achieved percutaneously over a guidewire using the Saldinger technique or with a small diameter introducer sheath. Alternatively, insertion is achieved by applying force to the skin and vessel of the patient with the tapered end of the repair assembly sufficient to gain direct entry into the vessel. This method of insertion is referred to herein as the "direct percutaneous" method of insertion.

The terms "superior" and "inferior" shall be used herein to have the same meaning as the terms "up" and "down" respectively and shall signify ends or directions which are towards and away from the patient's head, respectively. The terms "right" and "left" shall be used herein to signify ends or directions which are toward the patient's right and left sides, respectively. It should be noted that in the anatomical drawings provided herein, the patient faces the reader.

Figure 1:
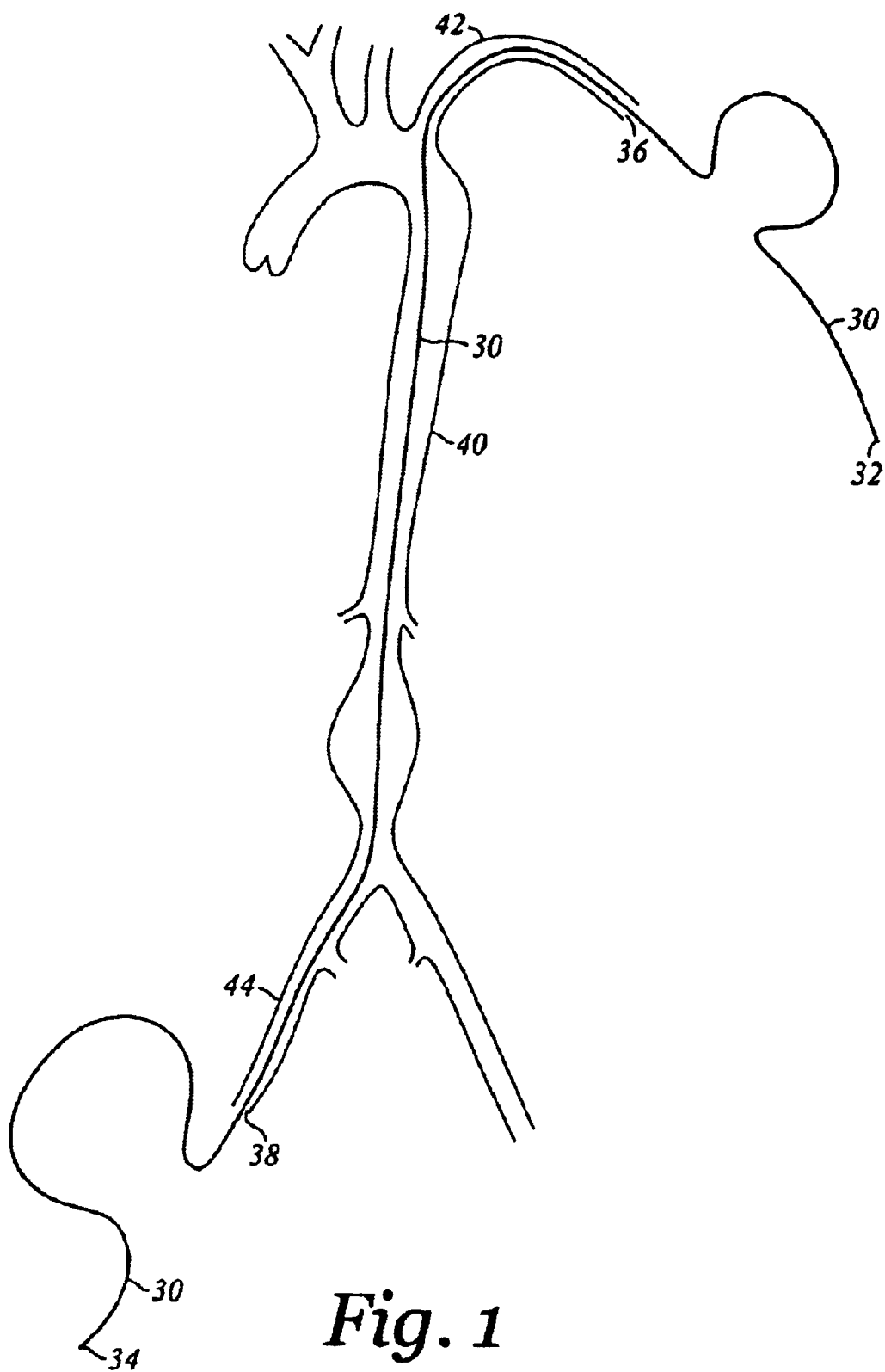
FIG. 1 is a sectional schematic view of the vascular system of a patient, showing the relationship of the aorta to the renal, axillary, iliac and femoral arteries, and also showing a guidewire configured to run between access points in the left axillary and the right femoral arteries.

As exemplified in FIG. 1, implantation of a straight or tapered graft according to the preferred embodiment of the present invention includes the use of a guidewire 30 with an superior end 32 an inferior end 34, which is configured to run between two access points of the patient's vascular system. In the preferred embodiment, if the vascular structure to be repaired is the aorta 40, the first access point 36 is in the left axillary artery 42 and the second access point 38 is in the right femoral artery 44. Additionally, the insertion of all elements of repair is accomplished by percutaneous or direct percutaneous insertion in the preferred embodiment. In other embodiments, the right axillary or the left femoral artery may be used, or alternatively any points of access on opposite sides of the defective vascular structure may be used.

Figure 2A:
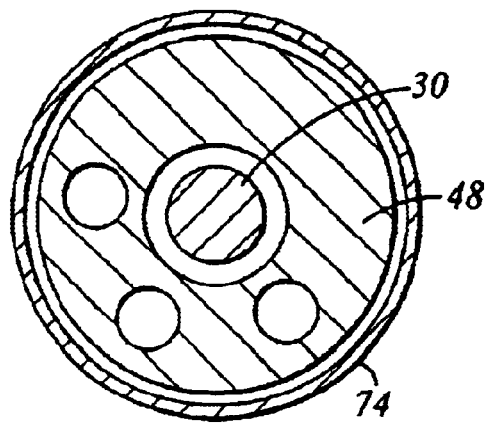
FIG. 2a is a section through the upstream catheter, sheath and guidewire of FIG. 2.
Figure 2:
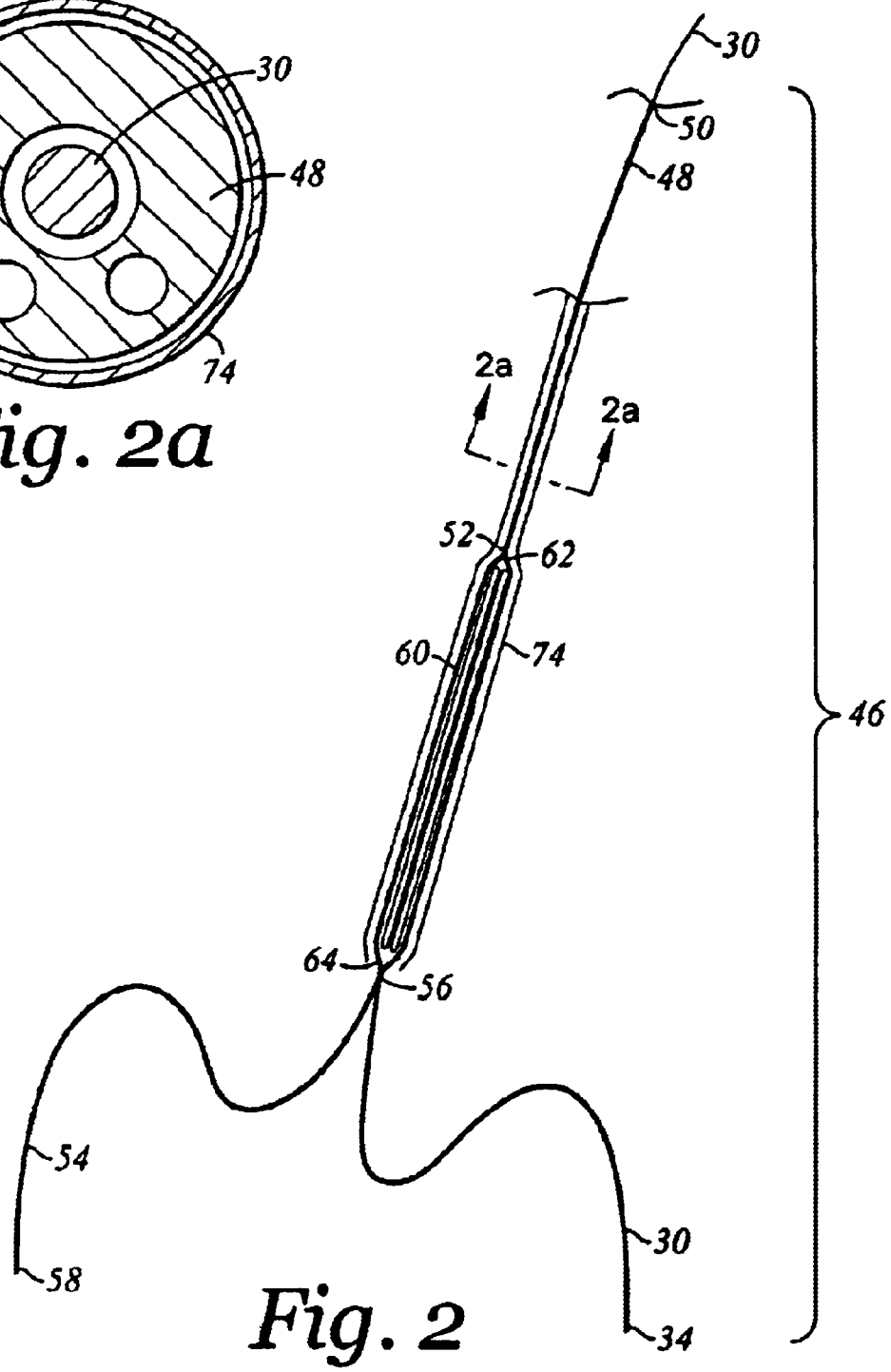
FIG. 2 is a perspective view of the repair assembly, showing the graft compressed by a sheath; also shown are the relative positions of the upstream and downstream traction catheters and guidewire, prior to insertion into the vascular system.
Figure 3:
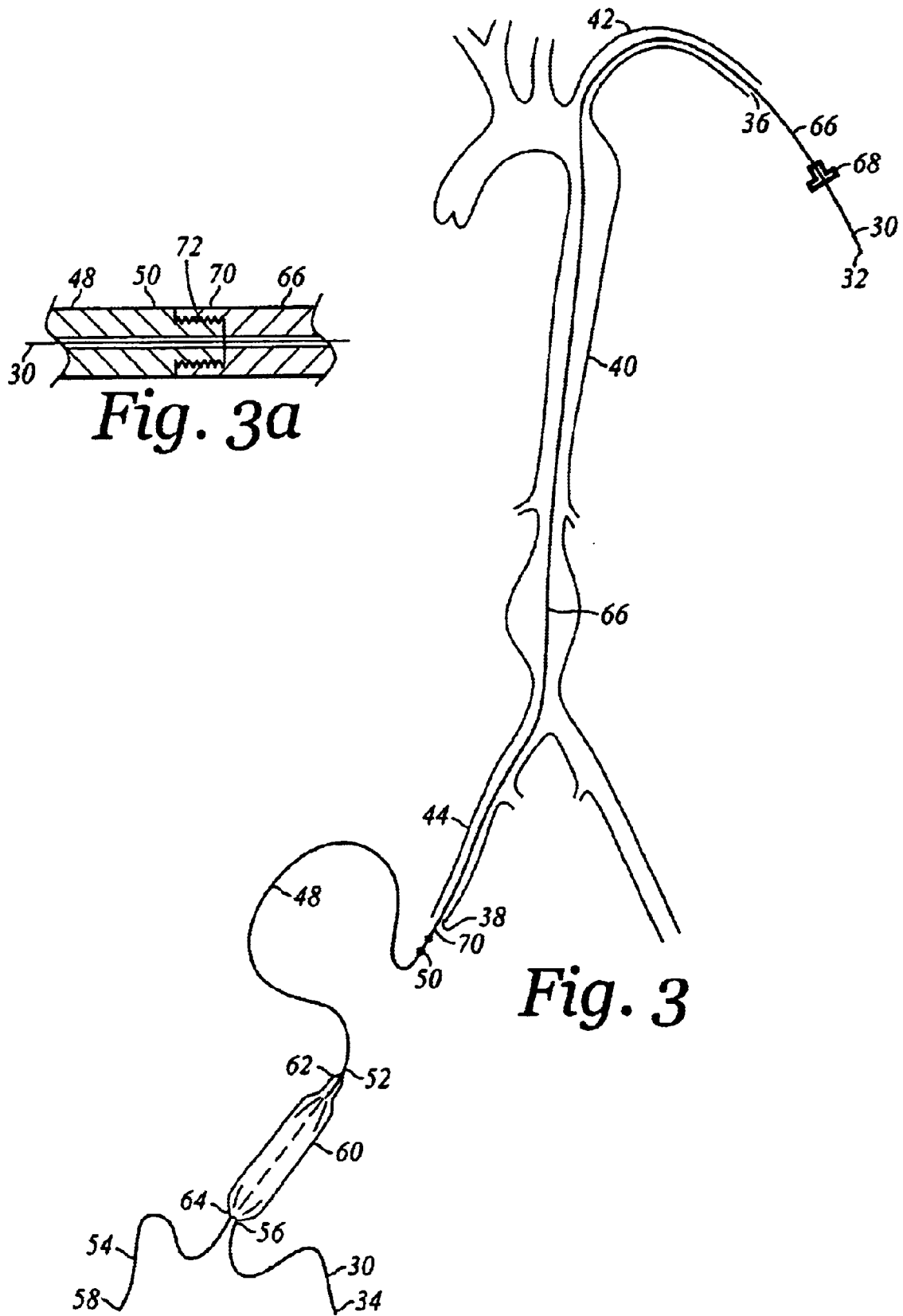
FIG. 3 is a schematic view showing the guidewire of FIG. 1 threaded downwards through an upstream traction catheter, through the bore of a tubular graft, and exiting the graft at its inferior end; a collection catheter is also shown, threaded over the guidewire from the first access point.

As exemplified in FIGS. 2, 2a and 3, in the preferred embodiment of the present invention, a repair assembly 46 is provided, comprising an upstream traction catheter 48 with a superior end 50 and an inferior end 52 and having a plurality of internal lumens; a downstream traction catheter 54 with a superior end 56 and an inferior end 58 and having a plurality of lumens, and; a graft 60 foldable radially between a compressed condition and an uncompressed condition and having a superior end 62 and an inferior end 64. In addition, the repair assembly includes a sheath 74, although it is also contemplated that the sheath can be omitted when it is desirable to do so.

Grafts are preferably formed from a biocompatible material having sufficient strength to withstand the implantation procedure described herein, and to endure the biomechanical forces that will be imposed on the graft. Such materials may include polyester materials such as DACRON, polytetrafluoroethylene, polyester materials, and silicone. Grafts are preferably made from material formed into woven fabric. The inferior end of the upstream traction catheter is releasably connected to the superior end of the graft. The superior end of the downstream traction catheter is releasably connected to the inferior end of the graft. There are numerous releasable connections known in the art.

The repair assembly 46 shown in FIG. 2 is assembled as follows. As exemplified in FIG. 3, when the guidewire 30 has been configured within the vascular system as described, protruding from the access points 36, 38, its inferior end 34 is threaded downwards first through a lumen of the upstream traction catheter 48 and then through the bore of the tubular graft 60. A tubular sheath 74, shown in FIG. 2, is configured to enclose and confine the graft 60 in a compressed condition, and to slidably disengage from the graft. (For the sake of clarity, the tubular sheath 74 is not shown in FIG. 3, but, if it had been shown at the stage of assembly exemplified in FIG. 3, it would be shown having been pulled upwards over the upstream traction catheter 48 prior to being pulled downwards over the graft 60 to hold the graft in compressed condition, as exemplified in FIG. 2.) In a preferred embodiment of the sheath, the sheath also slidably encloses the upstream traction catheter 48. In another embodiment, the sheath may enclose the downstream catheter 54 rather than the upstream catheter. In the preferred embodiment, the diameter of the sheath varies, having substantially one diameter extending over that portion of the sheath surrounding the graft, and having another smaller diameter extending over that portion of the sheath surrounding the traction catheter. In a further embodiment, the sheath may have a uniform diameter. Typical materials for forming the sheath include, for example, nylon, teflon, polytetrafluoroethylene, polythene and like materials. Before the graft is inserted in the vascular system, a portion of the sheath surrounding the upstream traction catheter is connected to the upstream traction catheter, thereby preventing relative axial movement between sheath and graft and preventing premature release of the graft.

Figure 4:
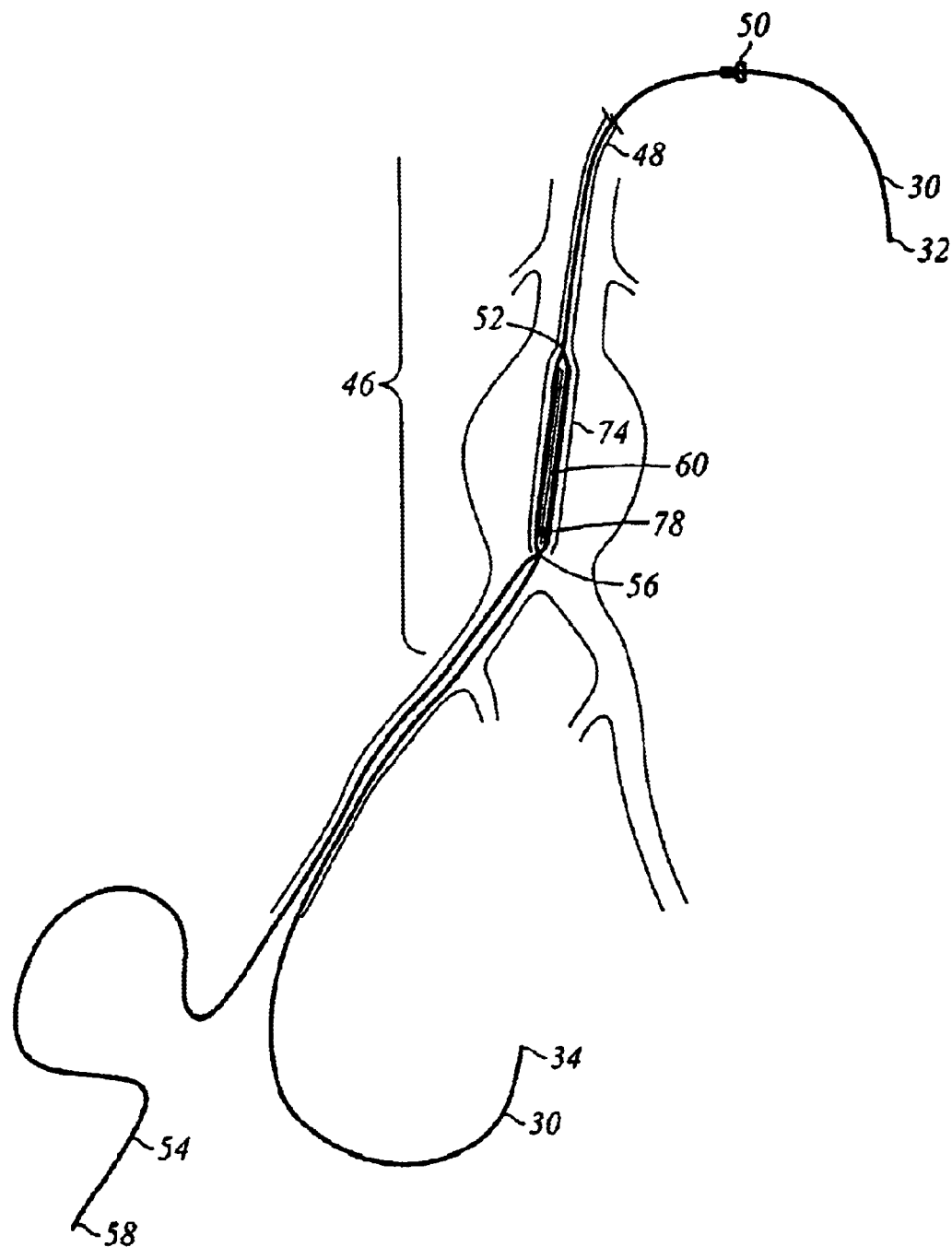
FIG. 4 is a perspective view of the repair assembly after it has been pulled superiorly by the upstream traction catheter until the graft is located in the aorta, shown here in section.

The upstream traction catheter 48 is then moved in a superior direction over the guidewire 30, eventually exiting through the first access point 36. This movement may be achieved by pushing the upstream traction catheter over the guide wire from the second access point 38 into the vascular system of the patient, until it protrudes from the first access point 36. Alternatively, as exemplified in FIG. 3, a collection catheter 66 with superior end 68 and inferior end 70 may be passed over the guidewire from the first access point until the collection catheter protrudes from the second access point. The inferior end of the collection catheter is then releasably connected to the superior end 50 of the upstream traction catheter 48 using any means of connection which is known in the art. A preferred means of releasable connection is to screw the inferior end 70 of the collection catheter to threads 72 provided on the superior end of the upstream traction catheter, as exemplified in FIG. 3a. The collection catheter is then withdrawn superiorly, through the first access point 36, thereby pulling the upstream traction catheter into the patient's vascular system, until it eventually protrudes from the first access point, whereupon the collection catheter is disconnected from the upstream traction catheter. Once either method described above has been used to advance the upstream traction catheter superiorly over the guidewire until its superior end protrudes from the first access point, differential tension may be applied to the upstream and the downstream traction catheters 48, 54 in order to introduce the graft into the desired position in the aorta 40, as exemplified in FIG. 4.

Figure 5:
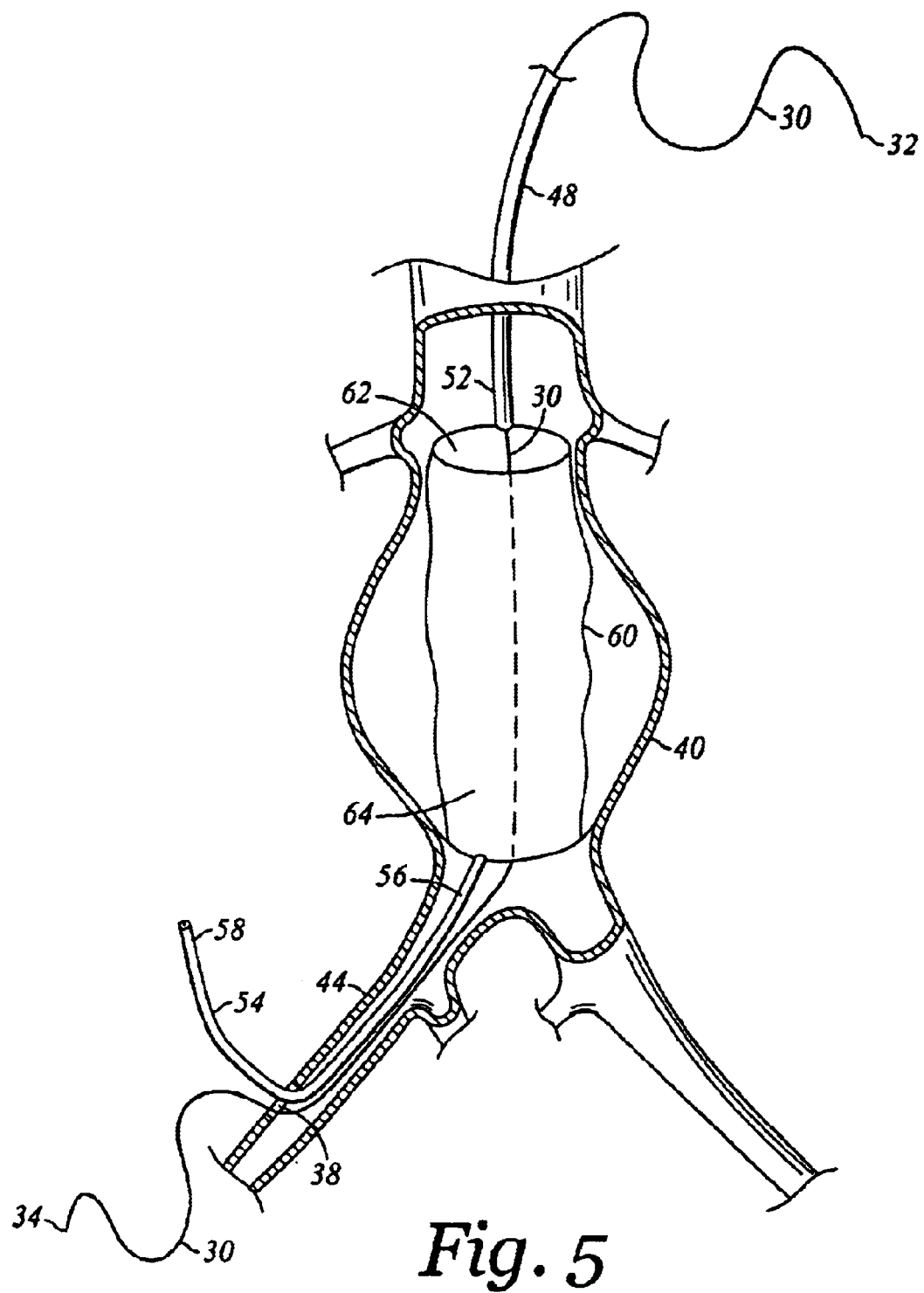
FIG. 5 is a perspective view showing the graft in an uncompressed condition within the aorta after the sheath has been withdrawn, while held in position by the upstream and downstream traction catheters.

The position of the repair assembly 46 and graft 60 within the vascular system may be ascertained by using flouroscopic methods that are known in the art. For example, a radio-opaque marker 78 may be attached to the inferior end of the sheath 74, as exemplified in FIG. 4. The marker may take the form of an annular ring formed from a metal, such as stainless steel or platinum-iridium, or may consist of any radio-opaque material. Once located in the desired position, the sheath is withdrawn by sliding it superiorly, over the upstream traction catheter and over the graft, thereby releasing the graft from its compressed condition and allowing it to revert to its uncompressed condition, as exemplified in FIG. 5. The graft may contain further radio markers to facilitate its final positioning.

Next, one or more attachment systems, compressible radially between a compressed condition and an uncompressed condition, are introduced into the bore of the uncompressed graft in order to engage the graft with the vascular wall. There are many types of attachment systems, or anchors, known in the art that will achieve the result of fixing the graft to the vascular wall. Such attachment systems may be self-expanding, may be manufactured from shape memory alloy such as Nitinol, and may include hooks or barbs. Alternatively, the attachment systems or anchors may be expandable by a balloon catheter.

Figure 6:
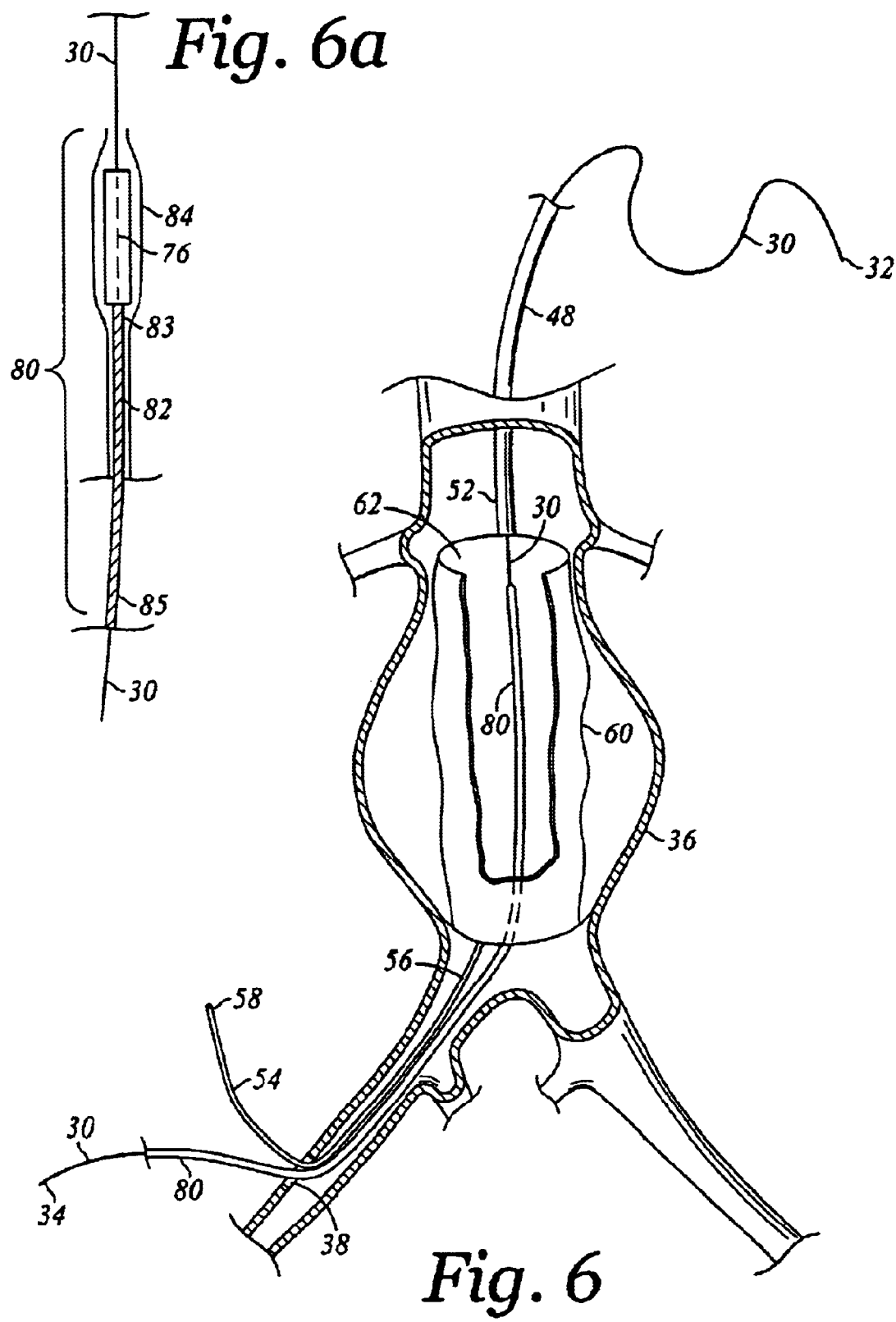
FIG. 6 is a perspective view of the graft (shown cut away) of FIG. 5, with a delivery assembly being introduced over the guidewire.

As exemplified in FIGS. 6 and 6a, the step of introducing an attachment system into the bore of the graft is achieved by inserting the attachment system into a delivery assembly 80 which is then introduced into the bore of the graft over the guidewire 30. As exemplified in FIG. 6a, the delivery assembly includes a pushrod 82 having superior end 83 and an inferior end 85 and at least one lumen, and a sheath or jacket 84 surrounding the pushrod and extending superiorly to provide a cover which applies a radially compressive force (if the attachment system is self-expanding) to the attachment system 76 which is releasably connected to the superior end of the push rod. In the preferred embodiment the diameter of the sheath varies, having substantially one diameter extending over that portion of the sheath surrounding the attachment system, and having another smaller diameter extending over that portion of the sheath surrounding the pushrod. The sheath may be manufactured from the same material as the graft sheath 74, and operates to first confine the attachment system in a compressed condition and then to release the attachment system when the sheath is slidably removed inferiorly over the pushrod 82. The attachment system 76 is delivered to the correct position within the bore of the graft by applying a superior force to the pushrod, which slides over the guidewire 30 to enter the bore of the graft 60.

Figure 7:
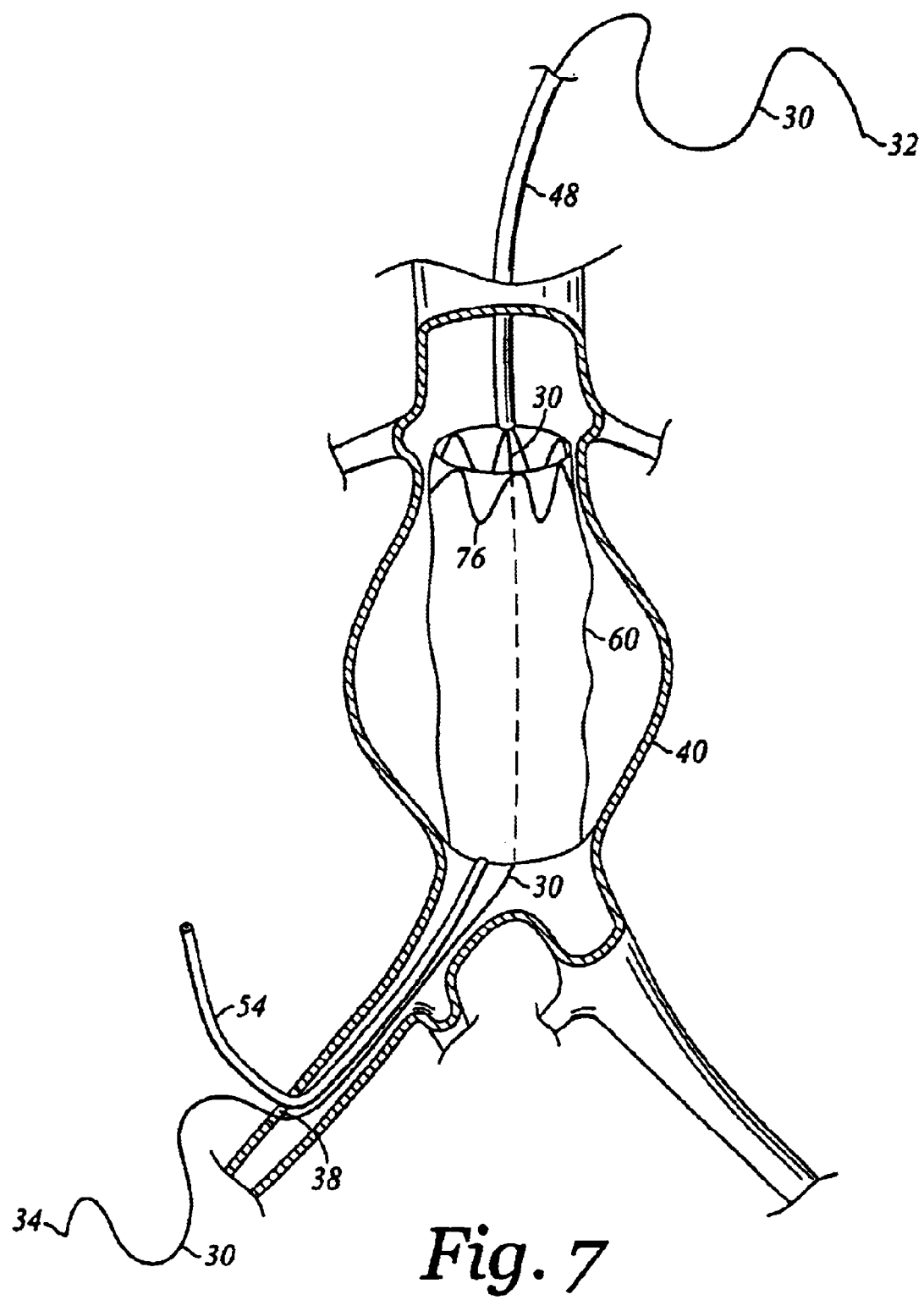
FIG. 7 is a perspective view of the graft of FIG. 6, in which the attachment system is shown in its expanded condition.

During insertion of the attachment system into the bore of the graft, the graft may be held in a fixed position by applying the appropriate tension forces to the two traction catheters 48, 54. When the delivery assembly 80 is being pushed over the guidewire 30, the sheath and the pushrod are connected to each other to prevent relative axial movement between the attachment system and the sheath, thereby avoiding premature expansion of the attachment system. The position of the attachment system in relation to the vascular structure may be determined by using flouroscopic methods such as those described above in relation to positioning the graft. When the attachment system has reached the desired position, the sheath is withdrawn by sliding it inferiorly over the pushrod while holding the pushrod in place. As exemplified in FIG. 7, withdrawing the sheath allows the attachment system 76 to expand radially (either as a self-expanding or balloon expanded attachment system) to an expanded condition in which it exerts an outward radial force on the graft 60 sufficient to attach the graft to the vascular wall 40. Such attachment may be either frictional or by means of barbs connected to the attachment system which penetrate the graft fabric and the vascular wall.

Figure 7A:
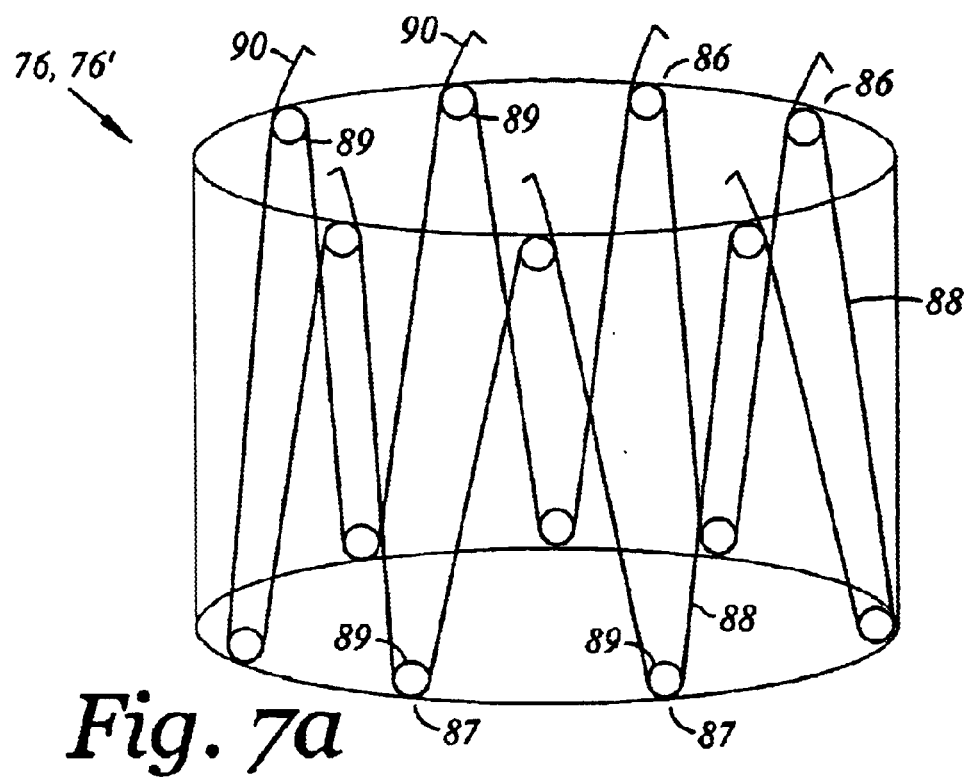
FIG. 7a is a perspective view of the embodiment of the attachment system shown in FIGS. 7, 14 and 15.

In one embodiment of a self expanding attachment system suitable for use with the present invention, an attachment system may be used which is made from a piece of wire which is bent in a generally undulating form and configured to have a generally cylindrical profile. This embodiment of self-expanding attachment system 76 is exemplified in a deployed state in FIG. 7 (and also as attachment system 76' in FIGS. 14 and 15), and is exemplified in full perspective in greater detail in FIG. 7a. The wire undulates between proximal apices 86 and distal apices 87 which are joined by connecting legs 88. At each apex, the wire may include a helical loop 89, to provide a greater range of expansion within the elastic range of the wire. Hooks 90 may be connected to each proximal apex by welding or gluing or other suitable connecting means, to enhance the ability of the attachment system to attach to the vascular wall.

Figure 7B:
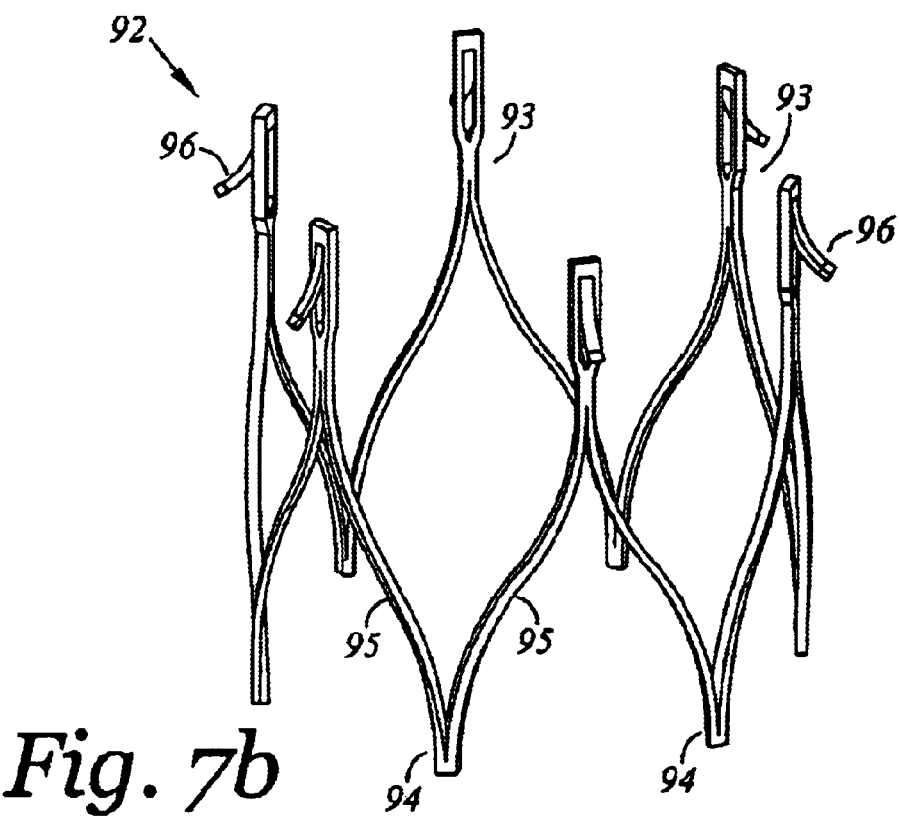
FIG. 7b is a perspective view of an alternative embodiment of an attachment system suitable for use with the present invention.

In another embodiment, an attachment system 92 suitable for using with the present invention, exemplified in FIG. 7b, may be manufactured from a continuous cylinder into which a pattern may be cut by a laser or by chemical etching to produce slits in the wall of the cylinder. The resulting structure may thereafter be heat set to give it a desired final configuration. The preferred final configuration includes a shape which undulates between proximal apices 93 and distal apices 94 which are joined by connecting legs 95. Hooks 96 may be added, either by shaping them from the continuous cylinder, or by welding or gluing them on.

It will be appreciated by one of skill in the art that, in the configurations of these previously described two embodiments, when the attachment system is compressed, its legs and apices are urged radially outward in a direction generally at right angles to its axis. Preferably, the self-expanding attachment systems of both described embodiments are made from a material having highly elastic properties such as nickel-titanium alloys, including Nitinol, since the same allows a great amount of expansion and compression of structures without permanent deformation. Implantable stainless steel is also known to be satisfactory for the purpose. An additional material from which such attachment system may be manufactured is Elgiloy™ which is a chromium-cobalt-nickel alloy manufactured and sold by Elgiloy of Elgin, Ill.

It will be appreciated that, as long as the guidewire 30 protrudes from the second access point 38 and runs within the bore of the uncompressed graft 60, and the traction catheters 48, 54 remain releasably connected to the graft, a plurality of attachment systems may be sequentially inserted within the bore of the uncompressed graft in the manner described above.

Once the required number of attachment systems have been deployed within the graft, the traction catheters are released from their connection to the graft and are removed together with the guidewire, leaving the graft fixedly supported by the attachment systems within the vascular system.

Figure 8:
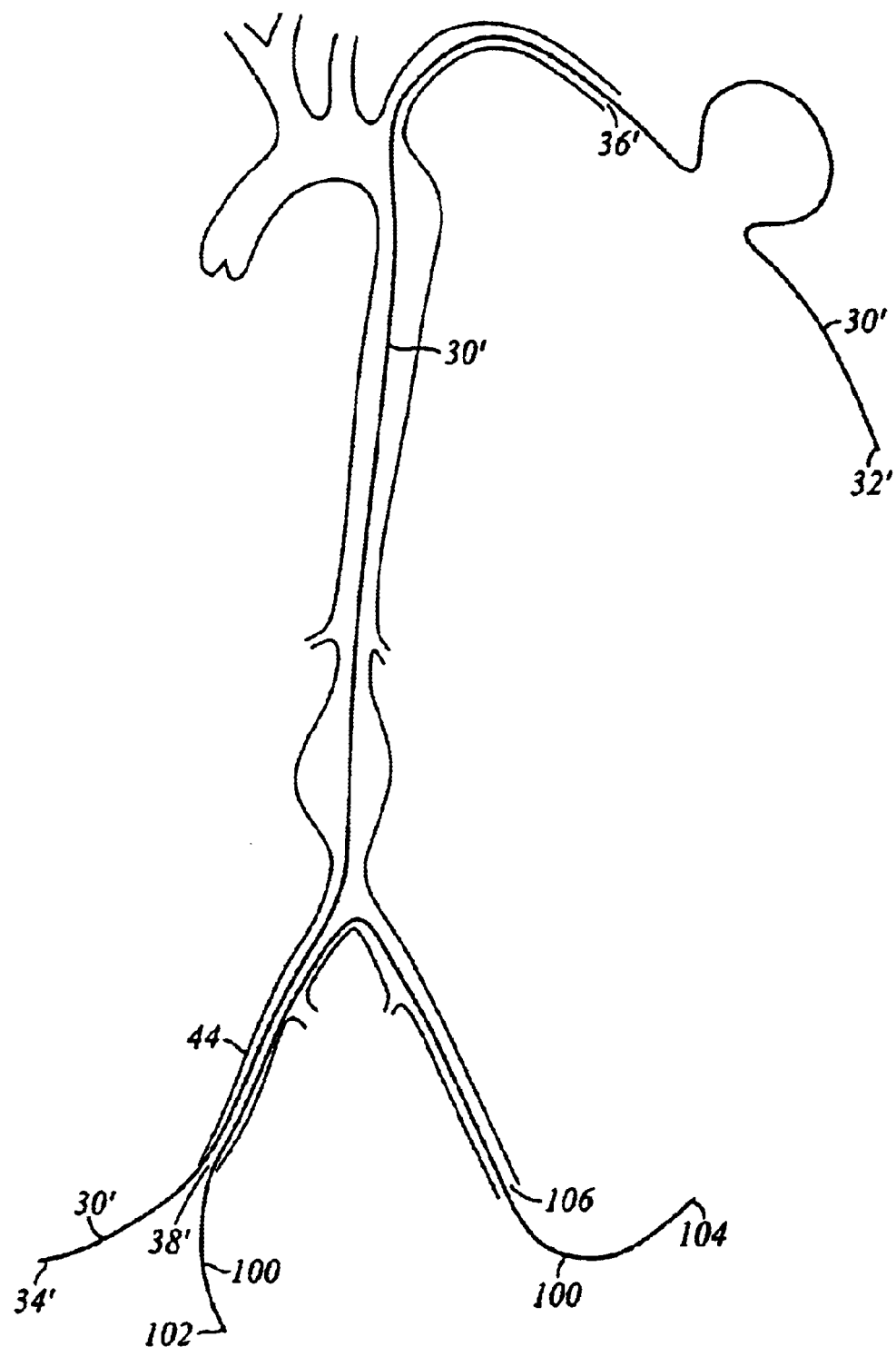
FIG. 8 is a sectional schematic view of the vascular system of a patient, showing the relationship of the aorta to the renal, axillary, iliac and femoral arteries, and also showing a first guidewire and a second guidewire configured to run between access points in the arteries.

Although the description of the aspect of the present invention set forth above relates to the staged implantation of a tubular or tapered graft, another aspect of the invention includes a device and method for the staged implantation of a bifurcated graft into a bifurcated vascular structure. As exemplified in FIG. 8, the method of implanting a bifurcated graft commences with placing within the vascular system a first guidewire 30' with an superior end 32' and an inferior end 34' and a second guidewire 100 with a right end 102 and a left end 104. In the preferred embodiment, if the vascular structure to be repaired is the aorta, the first access point 36' is in the left axillary artery and the second access point 38' is in the right femoral artery. In alternative embodiments, the right axillary or the left femoral artery may be used, or any points of access superior and inferior to the defective vascular structure may be used. In alternative embodiments, the steps set out below will have to be modified to accommodate the changes from left to right, and right to left, as may be necessary. In the preferred embodiment, the second guidewire is configured to run between the second access point and a third access point 106 in the left femoral artery.

Figure 10:
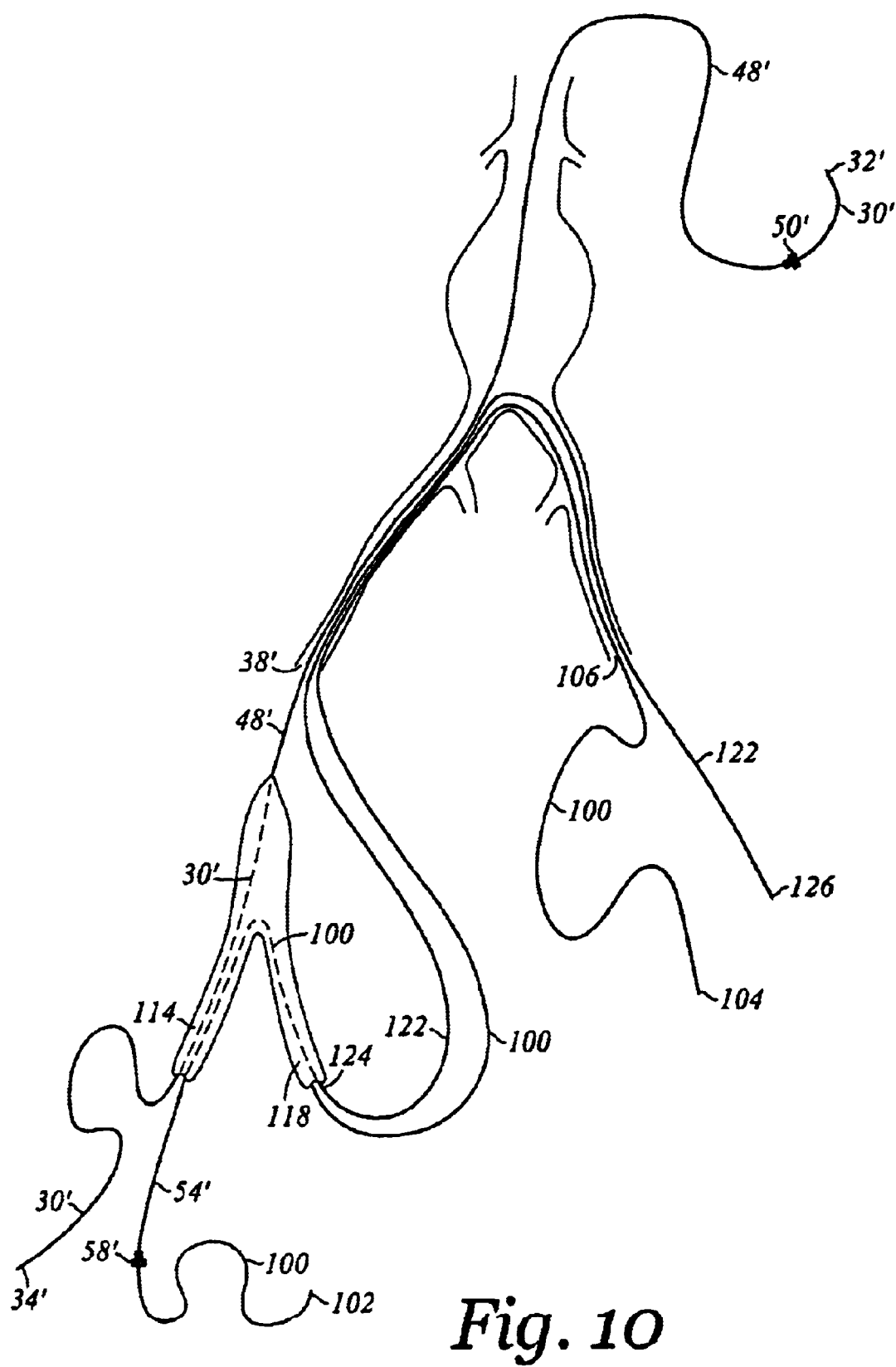
FIG. 10 is a schematic view of the assembly shown in FIG. 9, after the left downstream traction catheter has been configured to run between the second and third access points.
Figure 11:
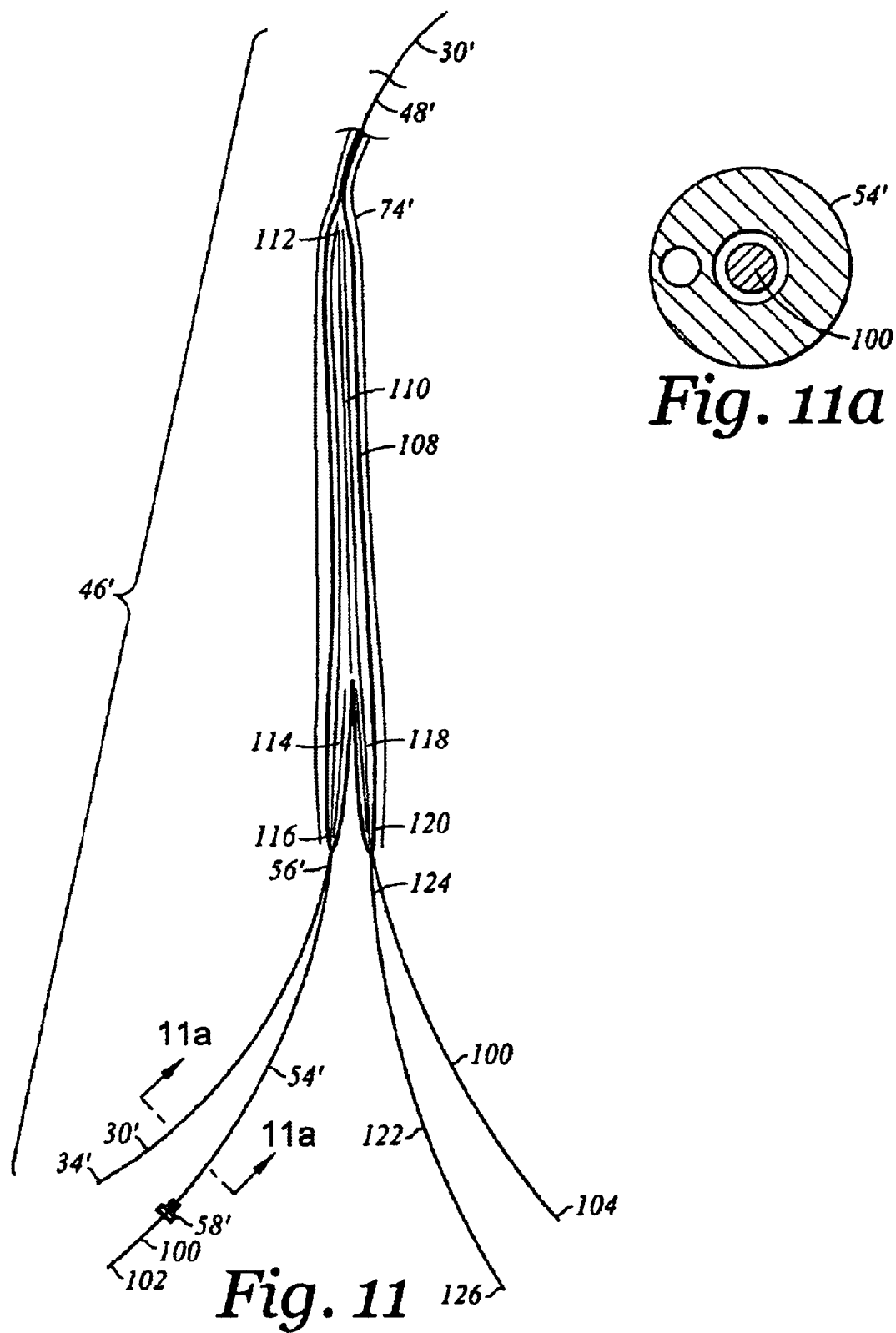
FIG. 11 is a perspective view of the bifurcated graft shown in FIGS. 9 and 10, after it has been enclosed by a sheath confining the graft in a compressed condition.

Then, as exemplified in FIGS. 9, 10 and 11, a repair assembly 46' is provided and assembled, comprising an upstream traction catheter 48' with an superior end 50' and inferior end 52', and a bifurcated graft 108 having a superior trunk 110 with a superior 112 end, aright inferior leg 114 and a left inferior leg 118 each with inferior ends 116, 120. Additionally, aright downstream traction catheter 54' and a left downstream traction catheter 122 are provided, each with superior ends 56', 124 and inferior ends 58', 126 and having a plurality of lumens. The repair assembly also includes a sheath 74', although it is contemplated that the sheath may be omitted when it is desirable to do so. (For the sake of clarity, the sheath 74' is not shown in FIGS. 9 and 10, but, if it had been shown at the stage of assembly exemplified in FIGS. 9 and 10, it would be shown having been pulled upwards over the upstream traction catheter 48' prior to being pulled downwards over the graft 108 to hold the graft in compressed condition.) As exemplified in FIG. 9, the following steps are undertaken outside the patient's body to assemble the repair assembly: The inferior end 52' of the upstream traction catheter 48' is releasably connected to the superior end 112 of the graft's superior trunk 110. The superior end 56' of the right downstream traction catheter 54' is releasably connected to the inferior end 116 of the graft's right inferior leg 114. The superior end 124 of the left downstream traction catheter 122 is releasably connected to the inferior end 120 of the graft's left inferior leg 118. Then, still proceeding outside the patient's body, the inferior end 34' of the first guide wire 30', which at this stage is protruding from the second access point 38', is threaded downward first through a lumen of the upstream traction catheter, then downward through the bore of the graft 108, entering the graft at the superior trunk 110 and passing out of the graft through the right inferior leg 114. Next, the right end 102 of the second guidewire 100 is threaded first through the bore of the graft, entering the graft through the graft's left inferior leg 118 and exiting at the end of the right inferior leg 114, from where it may be threaded into a lumen of the right downstream traction catheter 54'. It is not essential that the second guidewire be threaded into a lumen of the right downstream traction catheter, but doing so helps prevent the guidewire from subsequently becoming twisted around the traction catheter.

It is desired that the left downstream traction catheter 122 and the second guidewire 100 be configured to enter the second access point 38', as exemplified in FIG. 10, and to protrude from the third access point 106 without being twisted around each other within the vascular system. In the preferred method of achieving this configuration, a relay catheter 128 (shown in FIG. 9) with a plurality of lumens 129 may be passed over the second guidewire, so that it protrudes from both second and third access points 38', 106. A sectional view of the relay catheter at this stage of the procedure is exemplified by FIG. 9a. The left end 126 of the left downstream traction catheter 122 is then passed from right to left through one of the open lumens 129 of the relay catheter, until the left downstream traction catheter emerges from the third access point 106, whereupon the relay catheter may be withdrawn leftwards from the vascular system to expose both the second guidewire 100 and the left downstream traction catheter 122 passing between the second and third access points 38', 106 as desired, without twisting, as exemplified in FIG. 10.

Before introducing the graft into the vascular system, the graft is enclosed in a sheath 74', which extends superiorly to slidably surround the upstream traction catheter 48', as exemplified in FIG. 11. As in the case of the sheath 74 used to deliver the straight or tapered graft, the sheath 74' used to deliver a bifurcated graft may have a varying diameter, and may be constructed from the same materials.

Having thus fully assembled the repair assembly 46', the upstream traction catheter 48', surrounded by the sheath 74', is then introduced into the vascular system at the second access point 38' until it protrudes from the first access point 36'. This result may be achieved in the same manner used to introduce the upstream catheter 48 in the case of the straight or tapered graft, that is, either by threading the upstream traction catheter upwards over the first guidewire or by passing a collection catheter downwards over the first guidewire, and releasably connecting the upstream catheter to the collection catheter before withdrawing the collection catheter upwards until the upstream traction catheter emerges from the first access point.

Figure 12:
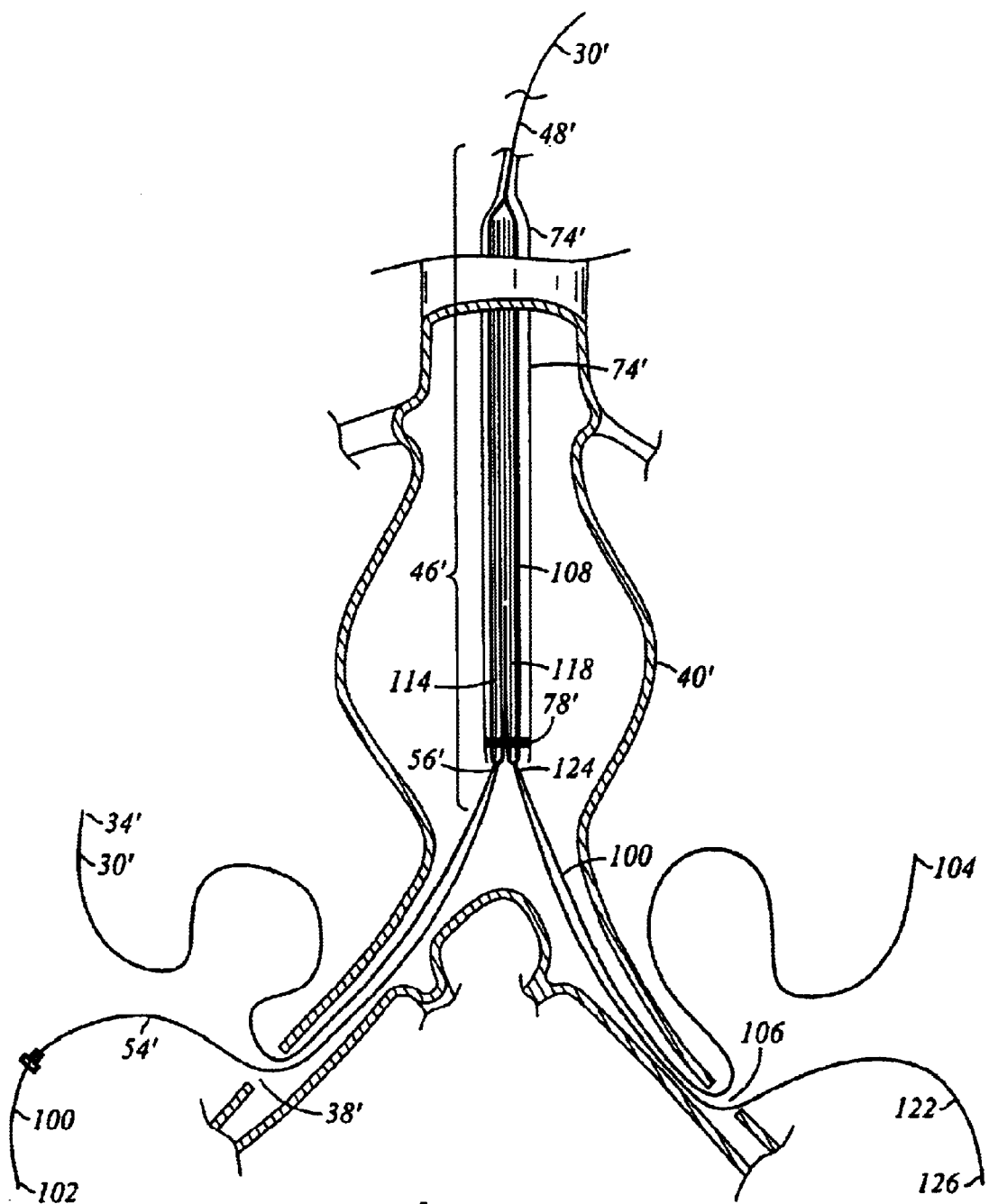
FIG. 12 is a perspective view of the graft in compressed condition within the aorta (shown cut away) before the graft is finally positioned, and showing the relationship between the graft, the sheath, the traction catheters and the guidewires.
Figure 13:
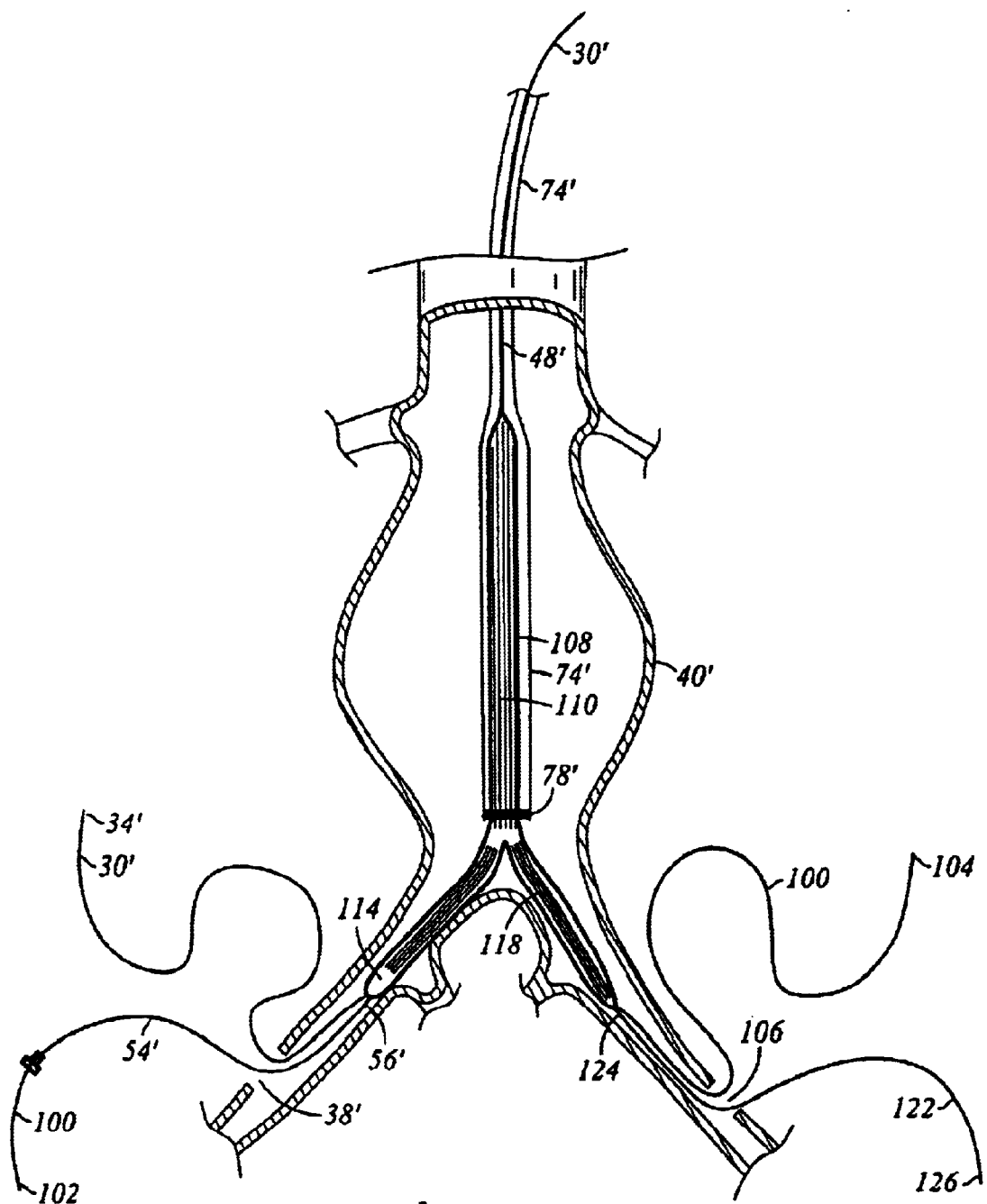
FIG. 13 is a perspective view of the bifurcated graft of FIG. 12, after the graft has been pulled inferiorly to allow the left and right inferior legs of the graft to enter the left and right iliac arteries respectively; a sheath is also shown, partially removed, confining the graft in a compressed condition.

As exemplified in FIG. 12, the next step is to draw the repair assembly 46' into the vascular system of the patient. This may be achieved by applying an superiorly directed traction force to the upstream traction catheter 48' until the bifurcated graft 108 in compressed condition is situated in the aorta with the inferior ends of the graft's inferior legs 114, 118 superior to the point of bifurcation of the aorta. Inferior traction forces may then be applied to the left and right downstream traction catheters 48', 122 until the graft is located in the desired position within the vascular system, as exemplified in FIG. 13.

Figure 14:
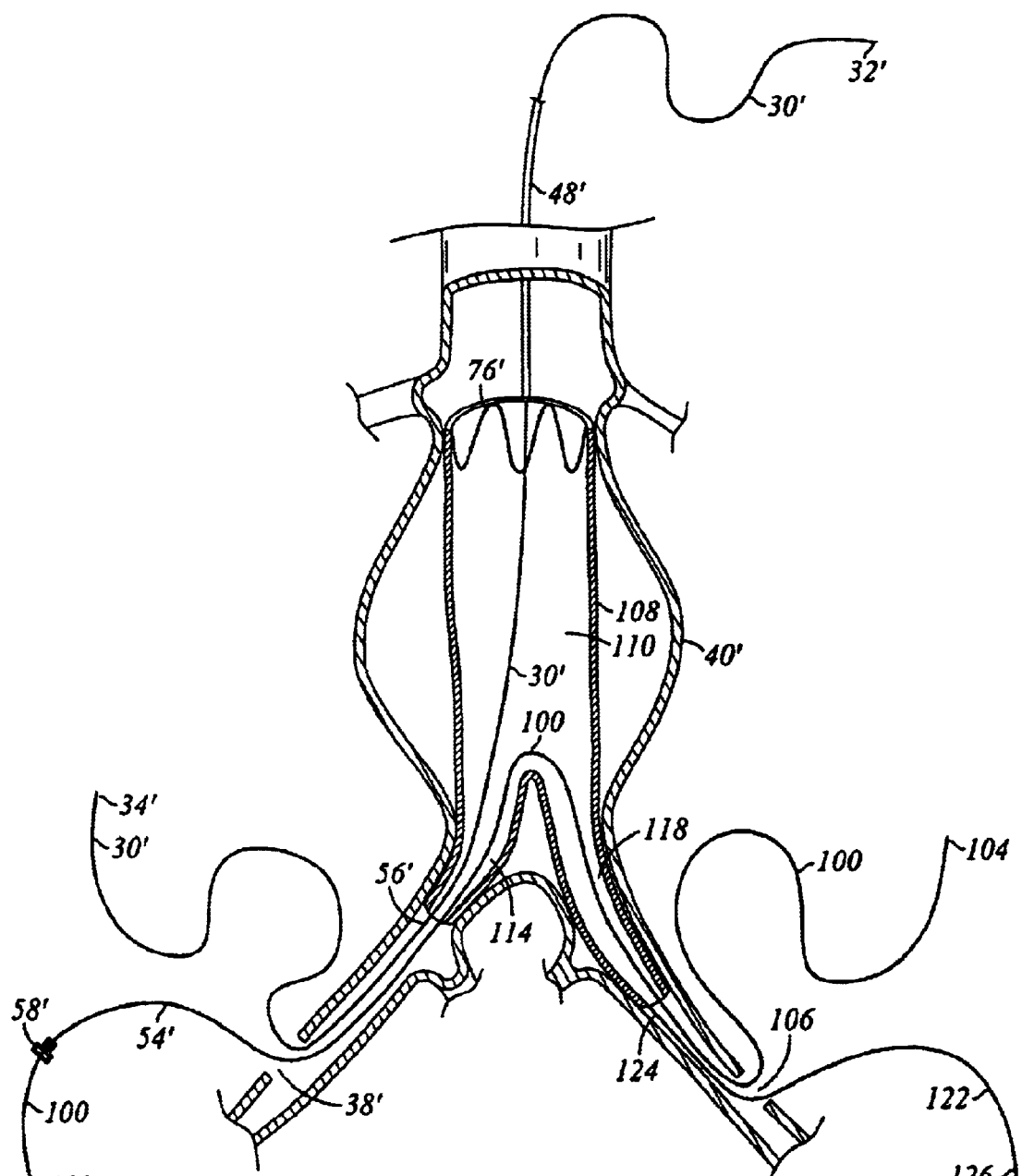
FIG. 14 is a perspective view (cut away) of the bifurcated graft of FIG. 13 after the sheath has been removed and after an attachment system has been deployed within the bore of the graft.
Figure 15:
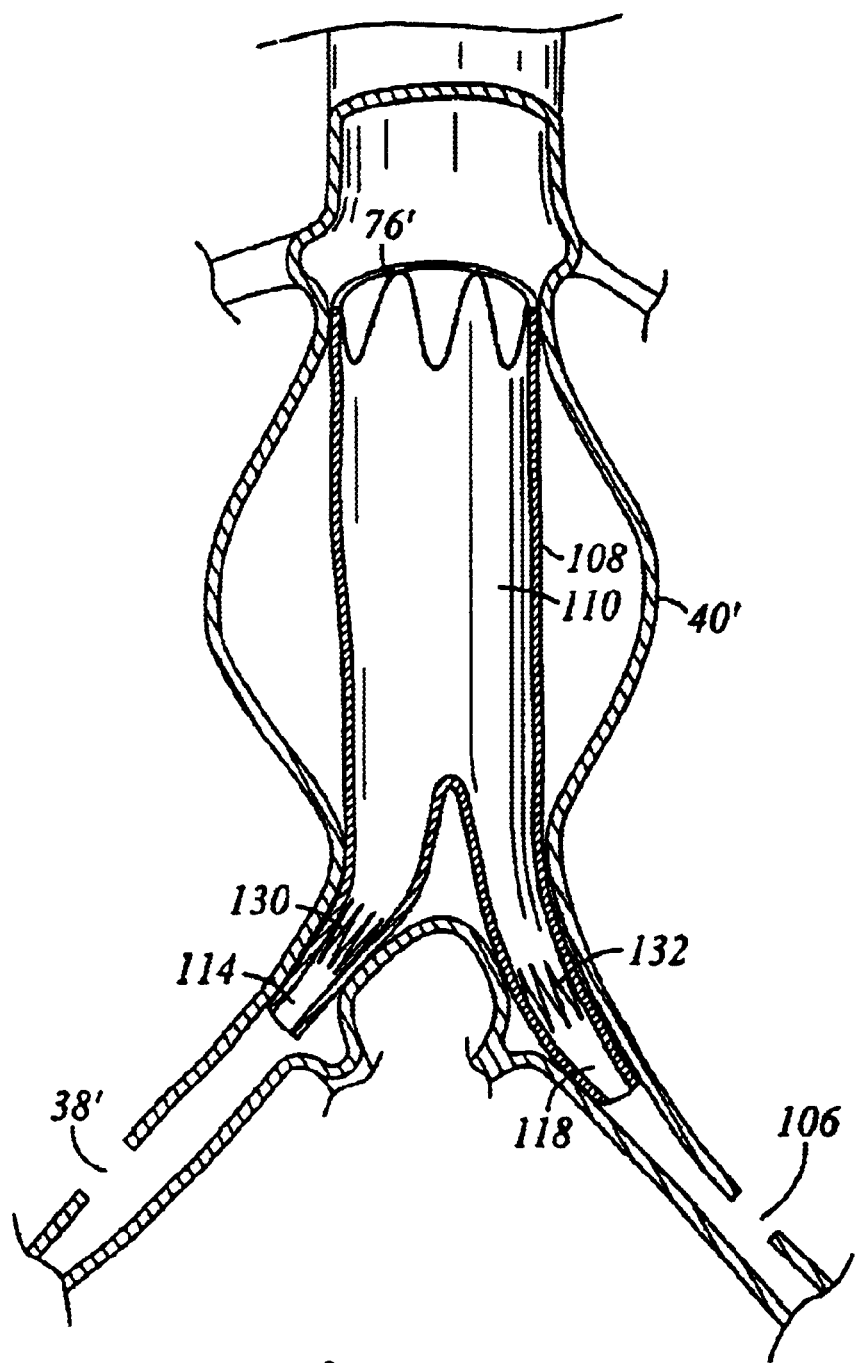
FIG. 15 is a perspective view (cut away) of the bifurcated graft of FIG. 14 with attachment systems deployed within the bore of the graft's superior trunk, and within the left and the right inferior legs.
Figure 16:
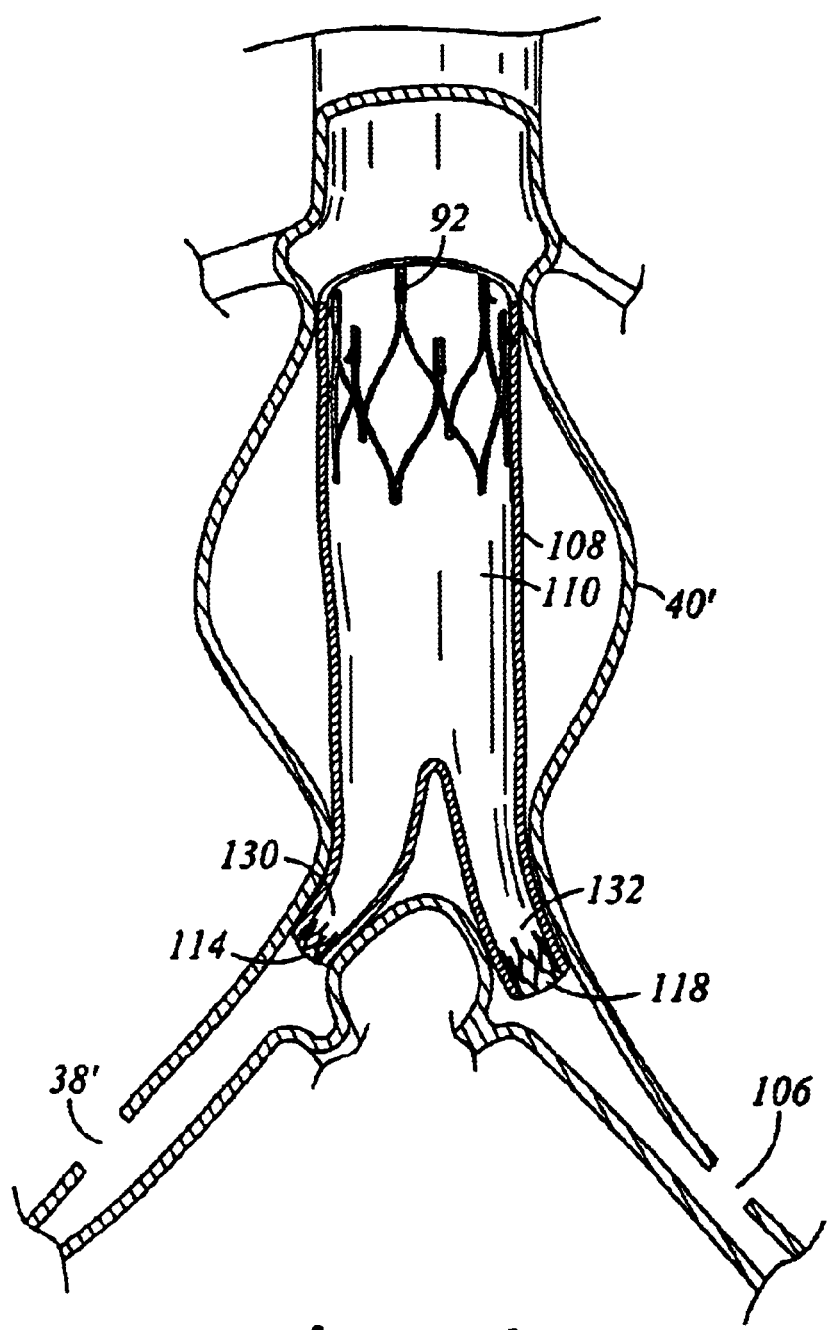
FIG. 16 is a schematic view (cut away) of the bifurcated graft of FIG. 15 shown in combination with the embodiment of the attachment system shown in FIG. 7b.

Once the bifurcated graft is located in a desired position within the aorta, the sheath 74' may be slidably removed by withdrawing it superiorly over the upstream traction catheter 48', allowing the graft to revert to its uncompressed condition, as exemplified in FIG. 14. Then, following a technique similar to that disclosed in the case of the straight or tapered graft above, at least one attachment system compressible radially between a compressed condition and an uncompressed condition is provided, and is fed into the vascular system in a compressed condition over the first or the second guidewire within a delivery assembly which includes a sheath or jacket to confine the attachment system in a compressed condition. Using the same flouroscopic technique as disclosed above, the attachment system is located at a desired position within the bore of the graft, and is then expanded or allowed to expand by removing the sheath. As exemplified in FIGS. 14 and 15, attachment systems 76', 130, 132 may be inserted over the first or the second guidewires into the bore of the graft 108. The graft may be maintained in a fixed position during delivery of the attachment systems by applying appropriate traction forces to at least two of the traction catheters, 48', 54', 122. Once the desired number of attachment systems have been positioned within the graft, the traction catheters are removed together with the guidewires, leaving the graft attached to the vascular wall. FIG. 16 exemplifies the graft 108 of FIG. 15, and shows the second embodiment of the attachment system 92 in, deployed position in the superior trunk and further embodiments of attachment systems 134, 136 in the inferior legs of the graft.

It will be apparent from the foregoing that, while particular forms of the invention have been illustrated and described, various modifications can be made without departing from the spirit and scope of the invention. For example, at the stage when an attachment system is fed into the vascular system over a guidewire, it is not essential to the invention that the guidewire protrude from the access point opposite to the access point into which the attachment system is fed. What is essential is that the guidewire should run into the bore of the graft through the appropriate inferior leg 114 or 118 (in the case of the bifurcated graft), and should extend upward into the bore of the graft as far as is necessary to implant the attachment system within the graft. For instance, the second-guide wire 100 may be repositioned by withdrawing it leftwards until its right end 102 is positioned in the left inferior leg 118 of the bifurcated graft, and by then pushing the guidewire upwards until its right end is positioned within the graft's superior trunk 110, or beyond. Such repositioning may assist in placing attachment systems within the left inferior branch of the bifurcated graft. Moreover, it is not essential to the invention that the graft be introduced through the second access point, but may equally be introduced through the third access point if the necessary changes are made to the points of entry/exit of the guidewires and traction catheters. Furthermore, while the preferred embodiment described above is used to implant a graft in the aorta, alternative embodiments may be used to implant a graft in any lumen of the body.

Furthermore, instead of using self-expanding attachment systems, balloon expanded attachment systems may be used.

Accordingly, it is not intended that the invention be limited, except as by the appended claims.

What is claimed is:

1. A method for the percutaneous insertion of a graft having a bore and being supported by at least one attachment system within the vascular system of a patient, the graft capable of assuming a compressed condition and an uncompressed condition, and the at least one attachment system being compressible and expandable radially between an expanded and compressed condition, the method comprising:

inserting the graft into the vascular system by direct percutaneous insertion;

applying a traction force to opposing ends of the graft to control the position of the graft within the vasculature, wherein the traction force is carried out using a plurality of catheters, each catheter configured to exert a force on the graft from a different point outside the vasculature;

positioning the graft adjacent a diseased portion of the vascular system;

subsequently inserting at least one attachment system into the graft in compressed condition by direct percutaneous insertion into a point of access to the vascular system over a propositioned guidewire;

positioning the at least one attachment system within the bore of the graft; and activating the at least one attachment system from its compressed condition to its expanded condition;

wherein the attachment system is implanted in the graft to form a seal between the graft and the vascular wall.

2. The method of claim 1, wherein the inserting step includes:

inserting the graft in compressed condition by direct percutaneous insertion into a point of access to the vascular system over a prepositioned guidewire; and activating the graft from its compressed condition to its uncompressed condition.

3. The method of claim 2, wherein the graft is configured to have a bifurcated profile having a superior trunk with a superior end and first and second inferior legs each with an inferior end, and wherein a first catheter having a first end and a second end is releasably connected by the first end to the superior end of the graft and configured so that the second end thereof extends through a point of access to the vasculature in the left axillary artery, a second catheter having a first end and a second end is releasably connected by the first end to the inferior end of the first leg and configured so that the second end thereof extends through a point of access to the vasculature in a first iliac artery, and a third catheter having a first and second end is releasably connected by the first end to the inferior end of the second leg and configured so that the second end thereof extends through a point of access to the vasculature in a second iliac artery.

* * * * *